United States Patent [19]
Fradet et al.

[11] Patent Number: 4,643,971
[45] Date of Patent: Feb. 17, 1987

[54] MONOCLONAL ANTIBODIES TO HUMAN BLADDER AND URETER CANCERS AND METHOD

[75] Inventors: Yves Fradet, Saint-Foy, Canada; Carlos Cordon-Cardo; Willet F. Whitemore, Jr., both of New York, N.Y.; Myron R. Melamed, Scarsdale, N.Y.; Lloyd J. Old, New York, N.Y.; Kenneth O. Lloyd, Bronx, N.Y.

[73] Assignee: Sloan-Kettering Institute, New York, N.Y.

[21] Appl. No.: 567,066

[22] Filed: Dec. 30, 1983

Related U.S. Application Data

[63] Continuation-in-part of Ser. No. 474,229, Mar. 11, 1983, abandoned.

[51] Int. Cl.[4] .......................... C12N 5/00; C12N 15/00; C12R 1/91; A61K 39/395
[52] U.S. Cl. .................................. 435/240; 436/548; 935/104; 435/172.2; 435/948; 530/387
[58] Field of Search ....................... 435/68, 172.2, 240, 435/241, 948; 436/548; 935/104; 260/112 R; 530/387

[56] References Cited

U.S. PATENT DOCUMENTS 4,363,799  12/1982  Kung et al. ........................ 435/68

OTHER PUBLICATIONS

Bubbers et al., "Monoclonal Antibodies to Human Tumor Associated Antigens on Transitional Cell Carcinoma", Federation Proceedings 41(3), p. 726 (1982).
Starling et al., "Monoclonal Antibodies to Human Prostate and Bladder Tumor Associated Antigens", Cancer Research 42, pp. 3084-3089 (1982).
Metzgar et al., "Antigens of Human Pancreatic Adenocarcinoma Cells Defined by Murine Monoclonal Antibodies", Cancer Research 42, pp. 601-608 (1982).

Primary Examiner—Charles F. Warren
Assistant Examiner—John E. Tarcza
Attorney, Agent, or Firm—Felfe & Lynch

[57] ABSTRACT

A panel of monoclonal antibodies, produced from human bladder tumors as immunogen, is used to diagnose the presence of transitional cell carcinoma in patients. The panel is also used to identify and differentiate low grade non-invasive papillomas from invasive life-threatening transitional cell carcinomas, thereby enabling decisions as to the extent of bladder surgery. These mAbs can also be used as a panel for tissue typing of normal and abnormal cell specimens.

10 Claims, No Drawings

MONOCLONAL ANTIBODIES TO HUMAN BLADDER AND URETER CANCERS AND METHOD

This invention was made in part with government support under CA 08748 and CA 21455 awarded by The National Cancer Institute. The government has certain rights in this invention.

This application is a continuation-in-part of copending application Ser. No. 474,229 filed March 11, 1983.

BACKGROUND

This invention concerns monoclonal antibodies recognizing human bladder cells. The monoclonal antibodies recognize antigenic markers on normal as well as cancerous bladder epithelial cells. Antibody specificity has been defined by reactions with cultured cells, and by reactions with normal adult and fetal tissues and malignant tissues. Capable of distinguishing normal versus low grade non-invasive versus high grade invasive cancers, these mAbs are useful in diagnosis and prognosis of bladder cancer. Tests with these mAbs enable surgeons to determine operative procedures in cases of bladder cancer.

In 1975 Köhler and Millstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Kohler-Millstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man and is relatively advanced. (See U.S. Pat. Nos. 4,361,549–550; 4,364,932–37 and 4,363,799 concerning mAb to Human T-cell antigens). Little is known about differentiation antigens displayed on normal and neoplastic cells belonging to other lineages.

This is due to the difficulty of obtaining a ready source of the appropriate normal cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982) U.S. patent application Ser. No. 469,854. This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma. Cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. Dippold et al. Proc. Nat'l. Acad. Sci. U.S.A. 77, 6114 (1980) and Houghton, et al. J. Exp. Med. 156, 1755 (1982) U.S. patent application Ser. No. 445,561. Immunoassay of melanocytes and melanoma cells within sub-sets is thus made possible.

Human astrocytoma mAbs have been produced by Cairncross et al (Proc. Nat'l Acad. Sci. U.S.A. 79, 5641 (1982) U.S. patent application Ser. No. 413,861.

SUMMARY

Bladder tissue must expand to hold excess urine. Bladder and ureter epithelial cells form an especially elastic tissue referred to as urotheluim or transitional epithelial cells. These cells can turn cancerous. One form of transitional cell carcinoma (TCC), papilloma, is a low-grade, non-invasive tumor which remains localized. Surgical treatment is usually limited to local excision of the tumor, since it never becomes invasive or metastatic i.e. life threatening. The bladder is saved thereby. Reccurrences are treated in like manner.

However, a second form of TCC is aggressive, invasive and metastatic. Surgical treatment indicated here is removal of the bladder. Together these two TCC cancers account for 95% of primary bladder cancer (bladder sarcoma is yet another form). It is important to distinguish between the two major TCC forms—the aggressive vs. non-aggressive—since the prognoses are radically different. Cytohistological methods to date are not always successful. A panel group of twelve mAbs of the present invention recognizing cancerous bladder cells enables such a distinction for differential diagnosis for the first time. In addition, the panel distinguishes normal from cancerous cells. Furthermore, the panel can be used for tissue typing in general. Samples of normal or abnormal tissues and/or cells are contacted with each of the monoclonal antibodies of the invention to determine tissue type. Antigen-antibody visualization techniques known in the art determine a positive reaction.

The invention thus comprises hybridoma cell lines producing mAbs recognizing human bladder cancer cell from the group of T16, JP165, J233, T23, T101, T43, T87, J143, T138, T110, Om5 and Om37 mAbs of the invention which recognize bladder glycoproteins having a molecular weight in the range of 25–240 kd (kilodaltons). The other antigens of the invention must then be glycolipids or proteins.

DESCRIPTION

Tissue culture. Cultured lines of human bladder cancer came from the collection of Dr. J. Fogh (Sloan-Kettering Institute). The derivation and maintenance of other established human cell lines and the short-term culture of normal skin fibroblasts and kidney epithelial cells have been described (Carey et al *Proc. Natl. Acad. Sci., U.S.A.* 73 3278–3282 (1976); Ueda et al *J. Exp. Med.* 150 564–579 (1979)).

Serological procedures. Rosetting assays for the detection of cell surface antigens using rabbit anti-mouse Ig or goat anti-mu chains conjugated to human O erythrocytes, were performed according to methods described previously (Dippold et al *Proc. Natl. Acad. Sci., U.S.A.* 77 6114–6118 (1980)). Absorption tests, assessment of heat stability of the antigenic determinants and Ouchterlony analysis of Ig subclasses were also performed as described (Cairncross et al *Proc. Natl. Acad. Sci., U.S.A.* 79 5641–5645 (1982); Carey, supra). Enzyme-linked immunoassays (ELISA) were carried out with adherent monolayer cells or with proteins in solid-phase (Lloyd et al *Immunogenet* 17 537–541 (1983)). For hemagglutination assays, see Anger et al *Hybridoma* 1 139–146 (1982).

Immunization. (BALB/c×C57BL/6)f$_1$ female mice were immunized 3–4 times at intervals of 3–4 weeks by intraperitoneal (i.p.) inoculation of $1 \times 10^7$ cells of T-24, 253-J, or 486-P and 253-J bladder cancer lines. For the derivation of Om Abs, a cell suspension was prepared from a bladder papilloma by mechanical dispersion and extracted with 0.5% Nonidet P-40 (NP-40) buffer. 100 micrograms of the papilloma extract was injected i.p. and 100 micrograms (in Freund's complete adjuvant) subcutaneously. After 4 weeks, an additional 100 micrograms of this extract was injected i.p.

Derivation of mouse monoclonal antibodies. Mice were sacrificed 3–4 days after the final immunization and spleen cells were fused with mouse myeloma MOPC-21 NS/1 cells as described (Cote et al *Proc. Natl. Acad. Sci., U.S.A.* 80 2026–2030 (1983)). Clones were initially selected according to their pattern of reactivity by ELISA on a panel of cultured cancer cells and normal kidney epithelium. Initial screening for Om Abs was carried out by indirect immunofluorescence on papilloma cell suspension attached to the wells of Falcon 3040 microtest II plates (Falcon Labware, Div. of Becton, Dickinson & Co., Oxnard, Calif.)(precoated with concanavalin A)(Mattes et al *J. Immunol. Meth.* 61:145 (1983). After subcloning 3–4 times, hybridomas were injected subcutaneously into nu/nu mice (Swiss background) and sera from mice growing tumors were used for serological and biochemical analysis of cultured cells.

Immunofluorescence assays. Frozen sections (5 micrometer) of tissues were fixed 5 min in 3.7% formaldehyde in phosphate-buffered saline (PBS), washed and incubated for 1 hr with undiluted hybridoma culture supernatants. The slides were washed and incubated for 30 min with a 1:40 dilution of flurorsceinconjugated goat anti-mouse Ig (Cappel Laboratories, Cochranville, PA), washed again and wet-mounted in 90% glycerol in PBS.

Immunoprecipitation procedures. Antibodies were tested for immunoprecipitating activity using detergent-solubilized cell extracts labeled by one of the following three methods: incorporation of [$^3$H]glucosamine or [$^{35}$S]methionine, or surface labeling with $^{125}$I (Dippold et al supra; Cairncross supra). NP-40 solubilization of cells and immunoprecipitation procedures using *Staphylococcus aureus*, have been described (Dippold supra; Cairncross supra). Molecular weight were determined under reducing conditions.

A preferred embodiment of the present invention is to test transitional cells shed into the urine of a patient with each of the monoclonal antibodies of the panel. The cells or part thereof are tested or contacted separately with each of the monoclonal antibodies in series dilution. Thus, an assay for cancer is possible with minimal patient disruption. Use of body fluids and exudates is preferable. Indeed, the present invention permits testing of human urine specimans for cell fragments containing antigenic markers for the monoclonal antibodies. Thus markers shed into the urine can be tested as well.

The present invention uses flow cytometric methods to assay for cell markers labelled by fluorescent monoclonal antibody.

The monoclonal antibodies of the present invention were prepared by an improved Kohler-Millstein procedure wherein spleen cells from a mouse (or other mammal) immunized with human cancerous bladder epithelial cells were fused with mouse myeloma to form hybridomas. By serological screening, antibodies from these hybridomas were found which recognize differentiation antigens on normal bladder and/or cancerous bladder. Other tissues, both normal and cancerous, may be recognized as well by some of these monoclonal antibodies.

A system of classification i.e. typing of normal as well as cancerous bladder tissue or cells based on these differentiation antigens is now possible, and serological assays for tumors of the bladder at various stages of differentiation or invasiveness using monoclonal antibodies to these markers has been developed. These assays are of special use in the early diagnosis of bladder tumors of the transitional epithelium. Significantly, they serve to differentiate low grade non-invasive papillomas from high grade invasive cancers of the bladder. A diagnosis of papilloma would indicate local excision of the tumor surgically whereas a diagnosis of invasive cancer indicates surgical removal of the bladder. Thus, prognosis for transitional cell carcinomas is possible for the first time using a panel of monoclonal antibodies of the invention. Aggressive TCC versus non-aggressive papilloma tumors can be distinguished with an accompanying decision as to the necessary extent of bladder surgery. The above serves as a preferred embodiment of the invention.

The assay of the present invention comprises contacting a tissue containing bladder cells with the antibody recognizing bladder cell antigens, preferably monoclonal antibodies to one or more cell antigens of the bladder antigenic system, and observing the immunoserological or immunopathological antigenic reaction between said monoclonal antibody and said antigen. In a preferred embodiment of the invention, the tissue sample to be contacted is ureter or bladder tissue and the antigenic reaction of the contacted tissue is observed by well known techniques such as immunofluorescence, radioactive mAb, rosette formation with sheep or human red blood cells linked to Protein A or to anti-immunoglobulin, direct absorption and the like.

In another preferred embodiment of the invention unknown human Cell specimens are analyzed for mAb reaction with each member of the cell panel using cell sorters for flow cytometry. Thus, the number of cells reacting with fluorescent mAb can be counted. The other well-known observation techniques can be employed to count the number of cells expressing the mAb antigen. In another embodiment of the present invention, the tissue to be assayed is first excised and is then either freshly, or after being frozen or embedded in paraffin by methods well-known in the art, contacted with the monoclonal antibodies of the invention. Observation of the reaction is as before.

In another preferred embodiment of the present invention, the tissue to be assayed comprises the intact body of an individual or a whole portion thereof. The antibody, tagged with a radioactive or other energy-producing element, is administered to the individual, and the whole body or part thereof is scanned externally for localization of radioactivity at the site of cancerous urothelial cells.

The present invention also makes possible the treatment of bladder tumors in a patient wherein the monoclonal antibody recognizing the cell antigen of cancerous transitional epithelial cells, preferably the cell differentiation antigen, is administered to the patient in an amount effective to inhibit the growth or proliferation of cancer cells. In a preferred embodiment of this method, the antibody is tagged with a potentially tissue destructive agent which causes destruction of the cancer cells. Examples of tissue destructive agents comprise chemotoxic agents, chemotherapeutic agents including vaccines, radionuclides, toxins, complement activators clotting activators and the like.

The examples are for illustrative purposes only and are not meant to limit the scope of the invention.

EXAMPLES OF ANTIBODIES, AND ANTIGENS RECOGNIZED

The following examples are intended to illustrate the invention without limiting same in any manner especially with respect to substantially functional equivalents of hybridomas, monoclonal antibodies and cell lines described and claimed herein. Substantially similar mAb can be produced in accordances with the invention following procedures outlined in the application.

The mouse monoclonal antibodies generated in this series were derived from immunizations with 253-J bladder cancer cells (AbJ143 and AbJ233) or in combination with 486-P cells (AbJP165) or immunizations with T24 cells (Abs T16, T23, T43, T87, T101, T110, T138). MAb Om5 and MAb Om37 were derived from immunizations and initial screening with noncultured bladder papilloma. Antibody specificity was determined by direct and/or absorption tests on a panel of 75 established human cell lines and short-term cultures of fibroblasts and kidney epithelial cells (Table I and IA also see table II), as well as by immunofluorescence analysis of 50 normal fetal and adult human tissues (Table III, IIIA) and 43 tumor specimens (Table IV and IVA). Antigens detected by these antibodies were also characterized by immunoprecipitation tests performed as in the following example:

An autoradiogram was made of [$^3$H]glucosamine-labeled glycoproteins from lysates of T-24 bladder cancer cells immunoprecipitated by mouse monoclonal antibodies detecting cell surface antigens of bladder cancer and analyzed by NaDodSO$_4$/polyacrylamide gel electrophoresis (reduced samples). Tracks: a, nu/nu mouse serum (control); b, AbT138; c, AbT16; d, AbT87; e, AbT43; f, AbJ143; g, AbT110. Molecular weight markers in kilodalton (kD): myosin (200), Beta-galactosidase (120), phosphorylase (98), bovine serum albumin (68), ovalbumin (43), concanavalin A (26).

Absorption analysis is shown in Table V for mAb OM5, T16 and T43.

The following is a brief description of 11 antigenic systems defined by this panel of monoclonal antibodies. None are related to A, B, H/I or Lewis blood group antigens as determined by hemagglutination and absorption tests with A, B, O or neuraminidase-treated O (T antigen) human erythrocytes or by solid phase ELISA assays with purified blood group glycoproteins (antigens, A, B, H, I, Le$^a$, Le$^b$, X and Y).

EXAMPLE 1

Om5 antigenic system.

The pattern of reactivity of mAb Om5 and mAb Om37 is identical, suggesting recognition of the same antigen. In tests with cultured cells, the only Om+ cell types were 4 of 18 bladder tumors, SK-MEL-28 and CAPAN-2. Immunofluorescence tests with normal fetal and adult tissues (including normal urothelium) showed no Om reactivity. However, four of ten bladder tumors reacted strongly with mAb Om5 and each of the Om5+ tumors had a papillary morphology. No other tumor types xpressed Om antigen. The antigen detected by mAb Om5 is heat-labile (100° C. for 5 min) and sensitive to Pronase or trypsin, suggesting a protein, but neither mAb Om5 nor mAb Om37 immunoprecipitated a detectable component from extracts of [$^3$H]glucosamine, [$^{35}$S]methionine or $^{125}$I-labeled SK-MEL-28 cells or $^{125}$I-labeled extracts of immunizing papilloma.

T16 antigenic system. MAb T16 immunoprecipitated a glycoprotein complex of $M_r$s 48,000 and 42,000 from [$^3$H]glucosamine-labeled T24 lysates under both reduced and nonreduced conditions. This antigen was strongly expressed by most bladder and breast cancer lines, but not by melanoma, astrocytoma or renal cancer lines. In contrast, epithelial cultures from 9/12 normal kidneys were T16+. In fetal and adult tissues, T16 was detected on epithelial cells of distal and collecting tubules of the kidney, urothelium, prostate, breast ducts and pluristratified epithelia of skin, exocervix and esophagus. In accord with the pattern of T16 expression on cultured cells, specimens of cancers of bladder and breast were T16+.

T87 antigenic system mAb T87 immunoprecipitated a glycoprotein of $M_r$ 60,000. T87 antigen was expressed by most cultured cell types. In normal tissues of the urinary tract, reactions with mAb T87 were similar to those of mAb T16. However, mAb T87 did not react with pluristratified epithelia, whereas it did react with breast acini, endometrium, thyroid, colon and fetal thymocytes. Most human carcinomas, with the exception of renal cancer, were T87+. Tumors of neuroectodermal origin (melanoma, astrocytoma) were T87−, despite the fact that cultured lines of these tumors were strong expressors of T87.

J143 antigenic system. mAb J143 recognized a glycoprotein complex of 140, 120 and 30 kD. A previously described monoclonal antibody, mAb AJ2 (Mattes et al Hybridoma (in press)), also detects this complex. J143 was strongly expressed (titer $10^{-9}$) on virtually all cultured cells with the exception of lymphoblastoid cells. However, its distribution in normal adult and fetal tissues were restricted to kidney glomeruli, basal membrane of thyroid microglands and the basal cell layer of urothelium, skin and esophagus. All bladder tumors expressed J143 as did other epithelial tumors. Similar to findings with mAb T87, cultured renal cancers, melanoma and astrocytoma were strong expressors of J143, whereas noncultured specimens of these cancers were J143 negative.

T43 antigenic system. mAb T43 immunoprecipitated a glycoprotein of $M_r$ 85,000. T43 was widely distributed on most cultured cell types with the exception of fibroblasts. In normal tissues, it was found only in proximal tubules of the kidney and the basal cell layer of skin, exocervix and esophagus. Normal urothelium of adult or fetus was T43 negative. A subset of bladder and renal tumors were T43+. In contrast to the T43+ phenotype of breast, lung and colon cancers, benign tumors of these organs were T43 negative.

T23 antigenic system. This antigen was expressed by a limited number of cultured cell types. In normal tissues, T23 was not detected on urothelium or other epithelial cells, but was found on astrocytes, melanocytes, fibroblasts, smooth muscle, cartilage and mature T lymphocytes of peripheral blood, spleen, lymph nodes and thymic medulla. MAb T23 identified a subset of bladder and kidney cancers and was also reactive with several other tumor types. T23 was the only antigen in this series expressed by specimens of neuroectodermal tumors. MAbT23 identified a heat-labile determinant which could not be immunoprecipitated from [$^3$H]glucosamine, [$^{35}$S]methionine or $^{125}$I-labeled cell lysates.

T138 antigenic system. mAb T138 immunoprecipitated a glycoprotein of $M_r$ 25,000. T138 was expressed by a range of tumor cell lines and by cultured renal epithelium. In normal adult and fetal tissues, however, reaction with mAb T138 were restricted to endothelial cells. A subset of bladder cancer specimens expressed T138. Of 33 specimens of non-bladder tumors, T138 expression has been limited to one sarcoma, subpopulations of cells of two lung cancers, and lining cells of cystic areas in two breast tumors.

T110 antigenic system. mAb T110 immunoprecipitated a glycoprotein of $M_r$ 240,000. Cultured cells showed low surface expression of T110. However, spent media from a variety of cultured normal and neoplastic cells had high levels of T110 antigen, as demonstrated by solid-phase immunoassays. T110 was detected as a fibrillar staining in the extracellular matrix of all normal and malignant tissues tested. AbT110 does not react with purified human cellular or plasma fibronectin, as indicated by direct binding or inhibition assays.

JP165, J233 and T101 antigenic systems. MAbs JP165, J233 and T101 detected heat-labile determinants, but these antigens could not be identified in immunoprecipitation tests with radiolabeled cell lysates. They are, however, distinguishable by their pattern of reactivity with the cultured cell panel. No JP165, J233 or T101 expression could be detected in normal adult or fetal tissues. JP165 expression was essentially restricted to a small subset of bladder and renal cancers in tests of cultured cells and tumor specimens. In contrast to the expression of J233 on cultured bladder and renal cancer cell lines, no J233 expression was found on specimens of these or any other tumor type. T101 was more widely distributed than JP165 and J233 on cultured cells. With tumor specimens, however, T101 expression was confined to a subset of bladder cancers, a villous adenoma, and a breast cancer.

The monoclonal antibodies selected for use in the present invention were derived from spleen cells of mice immunized with papilloma membrane extracts or whole cells of invasive transitional cell carcinoma cell cultures, such as 253J and T24, by fusion methods well known in the art. The ratio of spleen to NS/1 myeloma cell is 2–5:1 for the fusion process. Hybridoma producing antibodies Om5 or Om37 and JP165 were incubated in 2-mercaptoethanol in HT not HAT; HAT was used for subsequent cloning of these cell lines. (H=Hypoxanthine, A=Aminopterin, T=thymidine) Dippold, Supra.

A group of monoclonal antibodies which were found to recognize specific cell antigens of bladder epithelial cells, was selected as the bladder panel. This panel and the antigenic systems recognized are given in Tables I-V. Heterogeneity of human transitional cell carcinoma is therein noted. The table data point out and define the heterogeneity of transitional cell carcinomas. Eleven distinct new antigenic systems of TCC are defined by these mAbs as determined by serological analysis with 18 bladder cancers, over 50 non-bladder cancers and over 20 normal human cell lines (Tables I, IA & II). Immunopathology was done on frozen sections of normal adult and normal fetal tissue (Tables III and IIIA) and on frozen sections of various tumors (Tables IV and IVA).

In general, Om 37 (or Om5) identifies low graded papillary cancer and papilloma i.e. a subset of bladder tumors. They are heterogenous in staining for TCC and negative for normal urothelium or invasive TCC. Indeed neither Om5 nor Om37 reacts with any normal adult or fetal human tissue. Om37 (or Om5) identify well-differentiated TCC i.e. subsets human TCC. Om5 is not detected in normal bladder urothelium or in any other normal or malignant human tissue.

T43 however identifies poorly differentiated, invasive TCC and is negative for papilloma and normal urothelium. T43 reacts with normal tissue of the proximal tubule of the kidney and basal epithelial cells of the esophagus, skin and uterine endocervix. Om37 (or Om5) and T43 stain mutually exclusive subsets of TCC.

T101 and JP165 are also subset markers for bladder cancer that are not detected in normal tissues. T16, T43, T87 and J143 (antigens represented on many cultured cells) are found in specific areas of the normal urinary tract and in a distinctive range of other normal and malignant cell types, e.g., T16 expression in pluristratified epithelium of skin, exocervix and esophagus. T138 antigen is also a common feature of cultured cell lines, but its expression in sections of normal tissues is restricted to endothelial cells. In contrast, T110 is poorly represented on cultured cells but can be detected in culture supernatants. Localization of T110 in normal tissues demonstrated it to be a component of the extracellular matrix. All determinants detected by this series of antibodies are heat-labile and not related to A B H/I/Lewis blood group antigens. Six of the antibodies immunoprecipitated glycoproteins from radio-labeled cell lysates: mAb T16 ($M_rs$ 48,42 kD), mAb T87 ($M_r$ 60 kD), mAb T43 ($M_r$ 85 kD), mAbJ143 ($M_r$ 140, 120, 30 kD) and mAbT110 ($M_r$ 240 kD).

Monoclonal antibodies T23, J233, JP165 and T101 detect antigens expressed on subsets of high grade bladder cancer lines, and variably on other cancer lines but are not expressed in normal cells either in vitro or in tissue sections with the exception of T23 which is expressed on some normal cells on tissue section (fibroblasts, some types of lymphocytes, melanocytes and astrocytes).

T16 recognizes a 48 kd glycoprotein (gp) expressed on normal urothelium and on almost all transitional tumor lines with the exception of highly undifferentiated ones. T87, J143 and T43 detect gp complexes present on almost all tumor cell lines with differential distribution in different organs. T138 reacts with a 25 kd gp antigen expressed on endothelial cells and several tumor lines and T110 detects a protein shed into the culture supernatant of tumor and normal cell lines.

The glycoprotein antigens range in size from approximately 25 kd to about 240 kd. JP165, J233, T43, T87, J143, T110 and Om5 and Om37 are gamma sub one immunoglobulin molecules whereas T16 is a gamma sub 2B, T101 is gamma Sub 2A), and T23 and T138 are mu immunoglobulins.

T16, T87 and J143 mAbs detect gp antigens distinguishable in terms of molecular weights and patterns of reactivity on normal epithelial cells. All three react with normal urothelium but J143 reacts only with cells of the basal layer. J143 antigen was also found on the basal layer of well-differentiated TCC and in all cells of more aggressive TCC.

T16 and T87 antigens were found on all TCC specimans, but poorly differentiated areas of some TCC specimans become negative for T16 (11 TCC) and T87 (6 TCC). Metastatic TCC is negative for Om37 and T16 but positive for T87, J143 and T43.

One primary sarcoma of the bladder was negative for antigens for T16, T87, Om37, J143 and T43. This indicates the selectivity of the panel for TCC.

Changes in surface antigens are associated with different stages of differentiation. Thus, this invention technique defines surface antigens associated with bladder cancer.

Standard panels of cultured cell lines have facilitated the generation and analysis of monoclonal antibodies to cell surface antigens of human cancer. These cell lines, which represents cells from a wide range of distinct differentiation lineages, provide relatively homogeneous cell populations for immunization and for serological and biochemical studies. An alternative strategy for generating monoclonal antibodies, and one that has not as yet been extensively used, is direct immunization with fresh tissues rather than cultured cells. Some antigens may be poorly expressed on cells in vitro and their existence missed if analysis were restricted to cultured cell populations. This appears to be the case with the Om antigen, which is only weakly expressed by bladder cancer cells in vitro, but is well represented on fresh specimens of papillary bladder tumors.

As the number of new antigens identified by monoclonal antibodies grows, there will be an increasing need for useful methods to compare and classify them. This can be done in a number of ways, including representation on cultured cell panels, pattern of expression on normal and malignant tissues, biochemical characterization, chromosomal assignment of coding sequences, etc., and as information of this sort becomes available for each of the antigens, a comprehensive classification system will be possible.

It is useful to distinguish antigens on the basis of wide, intermediate or restricted distribution on the cultured cell panel. Of the 11 antigenic systems of bladder cancer defined in this study, four represent widely distributed antigens (T87, J143, T43 and T138), four are antigens of intermediate distribution (T16, T23, T101 and T110), and three show restricted distribution (Om5, J233 and JP165) with preferential expression on cell lines derived from renal and bladder cancers. Extending the analysis of these antibodies to reactions with normal and neoplastic tissues allows us to compare antigen expression in cultured vs. noncultured cells, and permits study of cell types not represented in the cell panel.

Some antigens show a relatively direct correlation between expression in vitro and in vivo. T87, J143 and T43, for example, are broadly represented on cultured cells and this parallels their expression on a range of normal and malignant cell types. Another example is JP165, which shows a restricted distribution on cultured bladder and renal cancers, and this pattern is similar to the expression of JP165 in tumor specimens, where expression is limited to a subset of renal and bladder cancers. The T16 phenotype of bladder, renal and breast cancers also shows good concordance between cultured cell lines and tumor specimens; bladder and breast cancers are T16+ and renal cancers are T16−.

There are some discrepancies between antigen expression in cultured cells and in tissue sections. T101 and T138 are expressed by many cell types in vitro. In normal fetal and adult tissues, no T101 can be detected and T138 expression is restricted to endothelial cells. In tumor specimens, with the exception of bladder cancers, T101 and T138 expression is also more restricted than would have been predicted from results with cultured cells. (An opposite pattern, e.g., restricted distribution in vitro and broad distribution in vivo has not been observed.) In addition, a number of instances have been found, particularly evident in the case of renal cancer (see e.g., J143, T138) in which cultured cancer cells expressed antigen whereas specimens of the corresponding tumor type did not. An explanation for this discrepancy may be that antigen expression is proliferation-related and higher levels of these antigens would therefore be expected on rapidly proliferating cultured cells.

A number of the antigens defined in this study were found in bladder cancers in vitro and in vivo but were not detected on normal bladder urothelium. In most of these instances of apparent "tumor specificity" with regard to the normal tissue counterpart, the antigens have been found in other normal tissues. However, two antigens detected on bladder cancer in vitro or in vivo, Om5 (Om37) and J233, have not been found to be expressed by any cultured cells of normal origin or by normal adult or fetal tissues.

A frequent finding with monoclonal antibodies detecting cell surface antigens is the heterogeneity observed among cell lines derived from histologically similar tumor types. In the case of hematopoietic tumors (Foon et al *Blood* 60 1-19 (1982)) and melanoma (Houghton et al *J. Exp. Med.* 156 1755-1766 (1982)), where this has been investigated most thoroughly, the diversity in surface phenotype of tumors appears to reflect a corresponding diversity in the surface antigens of normal cells as they undergo progression through early, intermediate, and late stages of differentiation. Tumor subsets can be defined on the basis of these surface markers, and relating these surface markers to the biological behavior of tumors is an active area of interest. With the monoclonal antibodies generated in this study, bladder cancer lines and bladder cancer specimens can also be placed into distinct subsets. Current indications are that Om5 and Om37 identifies bladder tumors of low-grade malignancy, whereas T23, T43 and T138 characterize more aggressive tumors. Thus a method for differential diagnosis of bladder malignancies is made possible by the invention.

This following hybridoma lines are maintained on deposit at Sloan-kettering Institute for Cancer Research, 1275 York Avenue, New York, N.Y. 10021 under designations corresponding to the mAb produced by each hybridoma as follows: T16, JP165, J233, T23, T101, T43, T87, J143, T138, T110, Om37 and Om5. Said hybridoma lines have been deposited with the American Type Culture Collection, 1230 Parklawn Drive, Rockville, Md. 20852 under ATCC designations corresponding to the above Sloan-Kettering designations as follows:

Deposit date: Mar. 11, 1983

| Sloan-Kettering deposit No. | Corresponding ATCC deposit/ Accession No. |
| --- | --- |
| JP165 | HB8280 |
| T16 | HB8279 |
| J233 | HB8272 |
| T23 | HB8271 |
| T101 | HB8273 |
| T43 | HB8275 |
| T87 | HB8274 |
| J143 | HB8276 |
| T138 | HB8277 |
| T110 | HB8278 |
| Om37 | HB8233 |
| Om5 | HB8270 |

TABLE I

SEROLOGICAL REACTION OF MONOCLONAL ANTIBODIES PRODUCED FROM HUMAN BLADDER TUMOR IMMUNOGEN WITH VARIOUS HUMAN CANCER CELL LINES IMMUNIZING TUMOR: BLADDER

| Antibody | T16 | JP165 | J233 | T23 | T101 | T43 | T87 | J143 | T138 | T110 | Om37 | Om5 |
| --- | --- | --- | --- | --- | --- | --- | --- | --- | --- | --- | --- | --- |
| Immunizing Tumor: | T24 | 253J 486P | 253J | T24 | T24 | T24 | T24 | 253J | T24 | T24 | PAP | PAP |
| Ig class of antibody: | $\gamma 2B$ | $\gamma 1$ | $\gamma 1$ | $\mu$ | $\gamma 2A$ | $\gamma 1$ | $\gamma 1$ | $\gamma 1$ | $\mu$ | $\gamma 1$ | $\gamma 1$ | |
| gp Antigen detected: | gp48 | | | gp85 | | gp80 60 | gp60 | gp140 gp120 30 | gp25 | gp240 | | |
| CELLS TESTED | | | | | | | | | | | | |
| *Bladder Ca* | | | | | | | | | | | | |
| RT-4 | 3 | 0 | 0 | 0 | 0 | 2 | 3 | 3 | 2 | 2 | 1 | 1 |
| SW-780 | 3 | 0 | 0 | 0 | 1 | 2 | 3 | 3 | 1 | 2 | 2 | 2 |
| 5637 | 3 | 0 | 0 | 0 | 1 | 2 | 2 | 3 | 2 | 0 | 0 | 0 |
| 647-V | 3 | 0 | 0 | 0 | 3 | 3 | 3 | 3 | 2 | 2 | 0 | 0 |
| VMCUB-1 | 3 | 0 | 0 | 0 | 3 | 3 | 3 | 3 | 2 | 2 | 0 | 0 |
| 639-V | 3 | 0 | 0 | 3 | 3 | 3 | 3 | 3 | 2 | 2 | 0 | 0 |
| T24 | 3 | 0 | 3 | 3 | 3 | 3 | 3 | 3 | 3 | 2 | 0 | 0 |
| J82 | 3 | 0 | 3 | 2 | 3 | 3 | 3 | 3 | 3 | 2 | 0 | 0 |
| VMCUB-2 | 3 | 0 | 0 | 0 | 3 | 3 | 3 | 3 | 2 | 2 | 0 | 0 |
| 575-A | 3 | 0 | 0 | 0 | 0 | 0 | 0 | 3 | 2 | 0 | 0 | 0 |
| VMCUB-3 | 2 | 0 | 0 | 0 | 1 | 0 | 0 | 3 | 2 | 0 | 0 | 0 |
| J'O.N. | 3 | 0 | 1 | 0 | 1 | 2 | 3 | 3 | 3 | 0 | 1 | 1 |
| TCCSUP | 2 | 3 | 0 | 0 | 0 | 2 | 3 | 3 | 3 | 0 | 0 | 0 |
| SW-1710 | 1 | 3 | 0 | 0 | 0 | 0 | 0 | 3 | 2 | | 0 | 0 |
| 486-P | 1 | 0 | 0 | 0 | 0 | 0 | 0 | 3 | 1 | 0 | 1 | 1 |
| 253-5 | 0 | 3 | 3 | 2 | 0 | 3 | 3 | 3 | 3 | 2 | 0 | 0 |
| Scaber | 3 | 0 | 0 | 0 | 1 | 0 | 0 | 3 | 1 | 0 | 0 | 0 |
| SW-800 | 0 | 0 | 2 | 2 | 3 | 3 | 3 | 3 | 0 | 0 | 0 | 0 |
| *Breast Cancer* | | | | | | | | | | | | |
| MCF-7 | 3 | 0 | 0 | 0 | 3 | 3 | 3 | 3 | 0 | 2 | 0 | 0 |
| BT-20 | 3 | 0 | 0 | 0 | 0 | 2 | 3 | 3 | 1 | 0 | 0 | 0 |
| CAMA | 3 | 0 | 0 | 0 | 3 | 3 | 3 | 3 | 3 | 0 | 0 | 0 |
| AlAb | 0 | 0 | 0 | 3 | 3 | 3 | 3 | 3 | 0 | 0 | 0 | 0 |
| MDA-MB-231 | 3 | 0 | 0 | 0 | 2 | 3 | 3 | 3 | 2 | 0 | 0 | 0 |
| MDA-MB-361 | 3 | 0 | 0 | 0 | 3 | 3 | 3 | 3 | 2 | 3 | 0 | 0 |
| *Ovarian Cancer* | | | | | | | | | | | | |
| SW-626 | 3 | 0 | 0 | 0 | 0 | 3 | 3 | 3 | 2 | 0 | 0 | 0 |
| ROAC | 0 | 0 | 0 | 0 | 0 | 3 | 3 | 3 | 3 | | 0 | 0 |
| OV-3 | 3 | 0 | 0 | 0 | 3 | 3 | 3 | 3 | 2 | 2 | 0 | 0 |
| 2774 | 0 | 0 | 0 | 0 | 0 | 3 | 3 | 3 | 0 | 2 | 0 | 0 |
| *Uterine Cancer* | | | | | | | | | | | | |
| Shustack | 0 | 0 | 0 | 0 | 0 | 0 | 3 | | 0 | 0 | 0 | 0 |
| ME-180 | 3 | 0 | 0 | 0 | 1 | 2 | 0 | 3 | 3 | 0 | 0 | 0 |

TABLE I-continued
SEROLOGICAL REACTION OF MONOCLONAL ANTIBODIES PRODUCED FROM HUMAN BLADDER TUMOR IMMUNOGEN WITH VARIOUS HUMAN CANCER CELL LINES
IMMUNIZING TUMOR: BLADDER

| Antibody | T16 | JP165 | J233 | T23 | T101 | T43 | T87 | J143 | T138 | T110 | Om37 | Om5 |
|---|---|---|---|---|---|---|---|---|---|---|---|---|
| Astrocytoma | | | | | | | | | | | | |
| AJ | 0 | 0 | | 2 | 0 | 3 | 3 | 3 | 0 | 0 | 0 | 0 |
| U-251 | 0 | | | 2 | 0 | 3 | 3 | 3 | 2 | 2 | 0 | 0 |
| Sullivan | 0 | 0 | | 0 | 0 | 3 | 3 | 3 | 0 | 0 | 0 | 0 |
| T-98 | 0 | 1 | | 1 | 0 | 3 | 3 | 3 | 2 | 0 | 0 | 0 |
| Machicaw | 0 | 0 | | 0 | 0 | 3 | 3 | 3 | 2 | 0 | 0 | 0 |
| Gitter | 0 | 0 | | 0 | 0 | 3 | 3 | 3 | 0 | 0 | 0 | 0 |
| Melanoma | | | | | | | | | | | | |
| SK-MEL-28 | 0 | 0 | 0 | 1 | | 3 | 3 | 3 | 2 | 2 | 3 | 3 |
| Me Wo | 0 | 0 | 0 | 2 | | 3 | 3 | 3 | 3 | 0 | 0 | 0 |
| -37 | 0 | 0 | 0 | 0 | 0 | 3 | 3 | 3 | 2 | 2 | 0 | 0 |
| -19 | 0 | | | 2 | | 3 | 3 | 3 | 0 | 2 | 0 | 0 |
| -29 | 0 | | 0 | 2 | 0 | 3 | 3 | 3 | 0 | 0 | 0 | 0 |
| -33 | 0 | 0 | 0 | 0 | 0 | 3 | 3 | 3 | 0 | 2 | 0 | 0 |
| Renal Cancer | | | | | | | | | | | | |
| SK-RC-7 | 0 | 3 | 3 | 1 | 3 | 3 | 3 | 3 | 3 | 0 | 0 | 0 |
| -28 | 0 | 3 | 3 | 1 | 3 | 3 | 3 | 3 | 3 | 0 | 0 | 0 |
| -1 | 0 | 1 | 1 | 2 | 3 | 3 | 3 | 3 | 3 | 0 | 0 | 0 |
| -39 | 0 | 0 | 3 | 0 | 3 | 3 | 3 | | 3 | 0 | 0 | 0 |
| -44 | 0 | 3 | 3 | 2 | 3 | 3 | 3 | 3 | 3 | 0 | 0 | 0 |
| -45 | 0 | 1 | 3 | 0 | 0 | 3 | 3 | 3 | 3 | 0 | 0 | 0 |
| -26 | 0 | 0 | 0 | 0 | 0 | 3 | 3 | | 3 | 0 | 0 | 0 |
| -29 | 0 | 0 | 3 | 0 | 0 | 3 | 3 | 3 | 0 | 0 | 0 | 0 |
| -9 | 0 | 0 | 3 | 2 | 3 | 3 | 3 | 3 | 3 | 0 | 0 | 0 |
| -4 | 0 | 3 | 3 | 0 | | 2 | 3 | | 3 | 0 | 0 | 0 |
| -6 | 0 | 1 | | 1 | 2 | 3 | 3 | 3 | 3 | 0 | 0 | 0 |
| -8 | 0 | 1 | | | 3 | 3 | 3 | 3 | 3 | 0 | 0 | 0 |
| Colon Cancer | | | | | | | | | | | | |
| HT-29 | 0 | 0 | 0 | 0 | 1 | 3 | 3 | 3 | 3 | 0 | 0 | 0 |
| SW-1222 | 0 | 0 | 0 | 0 | 1 | 3 | 3 | 3 | 3 | 2 | 0 | 0 |
| SW-1417 | 0 | 0 | 0 | 0 | 1 | 3 | 3 | 3 | 3 | 0 | 0 | 0 |
| SW-48 | 0 | 0 | 0 | 0 | 2 | 2 | 3 | 3 | 0 | 0 | 0 | 0 |
| Tallevi | 2 | 0 | 0 | 0 | 1 | 2 | 3 | 3 | 3 | 0 | 0 | 0 |
| Lung Cancer | | | | | | | | | | | | |
| SK-LC-1 | 0 | 0 | 0 | 0 | 1 | 3 | 3 | 3 | 1 | 0 | 0 | 0 |
| -2 | 0 | 0 | 0 | 0 | 0 | 3 | 3 | 3 | 3 | 0 | 0 | 0 |
| -5 | 0 | 0 | 0 | 1 | 1 | 3 | 3 | 3 | 3 | 2 | 0 | 0 |
| -6 | 0 | 0 | 3 | 0 | 0 | 3 | 3 | 3 | 0 | 2 | 0 | 0 |
| -8 | 3 | 0 | 0 | 2 | 3 | 3 | 3 | 3 | 3 | 2 | 0 | 0 |
| -13 | 0 | 0 | 0 | 3 | 3 | 3 | 3 | 3 | 2 | 2 | 0 | 0 |
| Teratocarcinomas | | | | | | | | | | | | |
| Tera-1 | 0 | 0 | 0 | 0 | 0 | 3 | 3 | 3 | 0 | | 0 | 0 |
| Tera-2 | 0 | 0 | 0 | 0 | 0 | 0 | 2 | 3 | 2 | | 0 | 0 |
| 833-K | 3 | 0 | 0 | 0 | 2 | 3 | 3 | 3 | 3 | 0 | 0 | 0 |
| 577-MF | 0 | 0 | 0 | 0 | 0 | 3 | 3 | 3 | 0 | 0 | 0 | 0 |
| CAPAN-2 | 3 | 0 | 0 | 0 | 0 | 0 | 0 | 3 | 3 | 0 | 1 | 1 |
| SK-HEP-1 | 0 | 0 | 0 | 0 | 3 | 3 | 3 | 3 | 3 | 2 | 0 | 0 |

Legend to Table I
Serological reaction of bladder panel monoclonal antibodies with tumor cell lines of various tissues by rosette formation with human red blood cells conjugated with rabbit anti-mouse Ig (Dippold et al. Supra)
where 0 = no reaction
2 = reaction at less than 10,000 fold dilution antibody supernatant
3 = reaction at greater than 10,000 fold dilution antibody supernatant
If there was no reaction by the above test, the absorption test was done. If an antibody was negative for rosette formation but absorbed onto the test antigen system it was deemed to be a positive reaction such that
1 = reaction by absorption test is positve though a test for rosette formation is negative.
i.e. 0 test for rosette formation is further tested by the absorption test. Therefore, 0 on this table indicates no reaction by either absorption or rosette formation.

TABLE I.A
REACTIVITY OF MOUSE MONOCLONAL ANTIBODIES GENERATED AGAINST BLADDER TUMORS. SEROLOGICAL TESTS WITH CULTURED HUMAN CELLS.

| CELLS | Om5 $\gamma^{1*}$ | T16 $\gamma^{2B}$ | T87 $\gamma^1$ | J143 $\gamma^1$ | T43 $\gamma^1$ | T138 $\mu$ | T23 $\mu$ | JP165 $\gamma^1$ | T101 $\gamma^{2A}$ | J233 $\gamma^1$ | T110 $\gamma^1$ |
|---|---|---|---|---|---|---|---|---|---|---|---|
| EPITHELIAL CANCERS | | | | | | | | | | | |
| BLADDER | | | | | | | | | | | |
| RT-4, SW780 | ø ø | ● ● | ● ● | ●"●" | ● ● | ● ø | 0 0 | 0'0 | 0'ø | 0 0 | ● ● |
| 5637, 647-V, VM-CUB-1 | 0 0 0 | ●"●"●" | ● ● ● | ● ● " ● | ● ● ● | ● ● ● | 0 0'0 | 0 0'0' | ● ● ● " | 0'0'0' | 0'● ● |
| 639-V, T-24, J-82 | 0 0 0 | ●"●"●" | ●"●"●" | ●"●"●" | ●"●"●" | ● ● ● | ● ● ● | 0 0 0 | ●"●"● | 0 ● ● | ● ● ● |
| VM-CUB-2, 575-A, VM-CUB-3 | 0 0 0 | ●' ●"● | ●"0'0' | ●"● ● | ●"0'0' | ● ● ● | 0'0'0 | 0'0'0' | ● 0'ø | 0'0'0' | ●0'0' |
| J'O.N., TCCSUP, SW-1710 | ø 0 0 | ● ● ● | ● ● 0' | ●"●"● | 0'● ● | ● ● ● | 0 0'0' | 0'● ● | ø 0'0' | ø 0'0' | 0'0'0' |
| 486-P, 253-J | ø ø | ø 0 | 0'●" | ● ●" | 0'● | ø ●" | 0 ● | 0' ● | 0' ● | 0'.● | 0 ● |

TABLE I.A-continued
REACTIVITY OF MOUSE MONOCLONAL ANTIBODIES GENERATED AGAINST BLADDER TUMORS. SEROLOGICAL TESTS WITH CULTURED HUMAN CELLS.

| CELLS | Om5 γ[1]* | T16 γ[2B] | T87 γ[1] | J143 γ[1] | T43 γ[1] | T138 μ | T23 μ | JP165 γ[1] | T101 γ[2A] | J233 γ[1] | T110 γ[1] |
|---|---|---|---|---|---|---|---|---|---|---|---|
| SCABER, SW-800 | 0 0 | ●0' | 0'● | ●● | 0'● | ⌀ 0' | 0 ● | 0'0' | ⌀ ● | 0'● | 0'0' |
| RENAL | | | | | | | | | | | |
| SK-RC-7, -28, -1 | 0'0'0 | 0 0 0 | ●●● | ●''●''● | ●●● | ●●● | ⌀ 0 ● | ●' ''⌀ | ●●● | ●●⌀ | 0'0'0' |
| SK-RC-39, -44, -45 | 0'0'0 | 0'0 0 | ●●'● | ●''●'● | ●●● | ●●●'' | 0'⌀'0' | 0'●'⌀ | ●●0' | ●●0' | 0'0'0' |
| SK-RC-26, -29, -9 | 0 0'0 | 0'0 0' | ●''●''● | ●''●'● | ●●● | ●0'● | ⌀0 ● | 0'0'0' | ●●⌀ | ⌀●● | 0'0'0' |
| SK-RC-4, -6, -8 | 0 0 0 | 0'0 0 | ●''●'● | ●''●'● | ●●'● | ●●● | 0'⌀● | ●''⌀ ⌀ | 0'●● | 0'●0' | 0'0'0' |
| COLON | | | | | | | | | | | |
| HT-29, SW-1222 | 0 0 | 0 0 | ●● | ●''●'' | ●●'' | ●● | 0 0 | 0'0 | ⌀ ⌀ | 0 0' | 0'● |
| SW-1417, SW-48, SK-CO-10 | 0 0 0 | 0 0 ⌀ | ●●● | ●''●'● | ●''●● | ●0● | 0'0 0 | 0 0 0 | ⌀ ⌀⌀ | 0'0 0 | 0'● ● |
| LUNG | | | | | | | | | | | |
| SK-LC-1, -2, -5 | 0'0 0 | 0 0'0 | ●●● | ●●''● | ●●●'' | ⌀●● | 0 0 0 | 0 0 0 | ⌀●● | 0'0 0 | 0'0'● |
| SK-LC-6, -8, -13 | 0 0 0 | 0 ●''0' | ●''●● | ●''●'● | ●''●'● | 0●● | 0 ●● | 0 0 0' | 0 ●''●'' | ●''0 0' | ●●● |
| BREAST | | | | | | | | | | | |
| MCF-7, BT-20, CAMA | 0 0 0 | ●''●''●'' | ●''●●'' | ●''●'● | ●''●●'' | 0'●● | 0'0 0 | 0'0 0 | ●0●'' | 0'0 ⌀ | ●0 0' |
| AlAb, MDA-MB-231, -361 | 0 0 0 | 0' ●● | ●''●''●'' | ●''●'● | ●''●'' '' | 0'⌀⌀ | ●0 0' | 0'0 0 | ●''⌀⌀ | ⌀●0' | 0'0'0 |
| OVARIAN | | | | | | | | | | | |
| SW-626, OV-3 | 0 0 | ●'●'' | ●●'' | ●●'' | ●● | ●●'' | ⌀ 0' | 0 0' | 0'0' | 0 0' | 0'0' |
| ROAC, 2774 | 0 0 | 0'0' | ●''●'' | ●''●'' | ●●'' | ●0' | 0'0' | 0 0' | ●'● | 0 0' | ●● |
| UTERINE | | | | | | | | | | | |
| SK-UT-1, ME-180 | 0 0 | 0'● | ●0' | ●''●'' | 0'● | 0'● | 0'0' | 0'0' | 0'⌀ | 0'0' | 0'0' |
| PANCREATIC, HEPATIC | | | | | | | | | | | |
| CAPAN-2, SK-HEP-1 | ⌀ 0 | ●0 | 0'●'' | ●●'' | 0'● | ●● | 0'0' | 0'0 | 0'● | 0'0' | 0 |
| ASTROCYTOMA | | | | | | | | | | | |
| SK-MG-1, U-251, SK-MG-BQ | 0 0 0 | 0 0 0' | ●''●'● | ●''●'● | ●●''● | 0'●0' | ●⌀⌀ | 0'⌀ 0 | 0'0 0 | ⌀0 0 | 0⌀0' |
| T-98, SK-MG-13, SK-MG-14 | 0 0 0 | 0 0'0' | ●●''●'' | ●●''●'' | ●●● | ⌀●0' | ⌀⌀0 | ⌀0⌀ | 0 0 0' | 0'0 0 | 0'0'0' |
| MELANOMA | | | | | | | | | | | |
| SK-MEL-28, -37, -19 | ●0 0 | 0 0 0 | ●''●''● | ●''●''● | ●''●''● | 0●● | ⌀●0 | 0 0'0 | ● ⌀0 | 0 0 0 | ●0'● |
| SK-MEL-29, -33, MEWO | 0 0 0 | 0'0'0' | ●''●● | ●''●'● | ●''●● | 0'0'0' | ⌀●0' | 0 0 0 | 0 ⌀ ⌀ | 0 0 0 | ⌀0 ● |
| TERATOCARCINOMA | | | | | | | | | | | |
| TERA-1, TERA-2 | 0 0 | 0'0' | ●●● | ●● | ●0' | 0'⌀ | 0'0' | 0'0' | 0'0' | 0'0' | |
| 833-K, 577-MF | 0 0 | ●0' | ●''● | ●● | ●● | ●0' | 0'0' | 0 0' | 0 0' | 0'0' | 0'0' |
| LYMPHOBLASTOID CELLS+ | | | | | | | | | | | |
| EBV-B cells | | | | | | | | | | | |
| DX, AZ, BD | 0 0 0 | 0 0 0 | ⌀ ⌀ | 0 | ⌀ 0 | 0 0 0 | 0 0 0 | 0 0 0 | 0 0 0 | 0 0 0 | |
| AV, FG, AP | 0 | 0 0 | 0 ⌀ | 0 0 | ⌀ ⌀ | 0 | 0 0 | 0 0 | 0 0 | 0 | |
| NORMAL HUMAN CELLS | | | | | | | | | | | |
| KIDNEY EPITHELIUM | | | | | | | | | | | |
| KT, LN, KN, | | 0'0'● | ●0'● | ●''●'●'' | ●0'⌀ | ●●● | 0'0'0 | 0'⌀ 0' | 0'⌀ 0' | 0'0'0' | ●0'0' |
| LI, LJ, MN, | 0' | ●●● | ●●● | ●''●'●'' | ●●0' | ●●● | 0'0'0' | 0'0'0' | 0 0 0' | 0'0'0' | 0'0'0' |
| MQ, MP, MV, | 0'0'0' | ⌀●● | ●●● | ●''●''●'' | 0'⌀⌀ | ●●● | 0'0'0' | 0'0'0' | 0'0'● | 0'0'0' | 0 |
| MS, NO, NP, | 0'0'0 | 0'●● | ●●● | ●''●''●'' | 0'⌀ | ●●● | 0' ⌀ | 0 | 0' | | |
| NQ, NR, NS, | 0 0 0 | | | | | | 0 0 0 | ⌀ ⌀ ⌀ | ⌀ ⌀ ⌀ | 0 0 0 | |
| ADULT SKIN FIBROBLASTS | | | | | | | | | | | |
| KY, EU, | 0 0' | 0 0' | ●0' | 0 ●'' | 0 0' | 0 0' | ⌀ ⌀ | 0 0' | 0 0' | 0 0 | |
| JE, AG, | 0 0' | 0'0' | ●● | ●● | 0'0' | 0'0' | 0 0 | 0 0' | 0 0' | 0'0' | |
| ERYTHROCYTES | | | | | | | | | | | |
| A+, B+, O+ | 0 0 0 | 0 0 0 | 0 0 0 | 0 0 0 | 0 0 0 | 0 0 0 | 0 0 0 | 0 0 0 | 0 0 0 | 0 0 0 | |
| XENOGENEIC CELLS | | | | | | | | | | | |
| Sheep erythrocytes | 0 | 0 | 0 | 0 | 0 | 0 | D 0 | 0 | 0 | 0 | 0 |

*Antibody subclass determined by Ouchterlony test. +In the case of lymphoblastoid cells only absorption tests were performed.
Reactivity of monoclonal antibodies with individual cell lines is symbolized as follows:
● Titer >10[-6]
● Titer 10[-4] — 10[-6]
⌀ Titer 2 × 10[-2] – 10[-4]
● Direct test negative; absorption test positive
0 Direct test negative; absorption test negative
0'Direct test negative; absorption test not done

TABLE II
REACTION OF MONOCLONAL ANTIBODIES PRODUCED FROM HUMAN BLADDER TUMOR IMMUNOGEN WITH NORMAL HUMAN CELL LINES
IMMUNIZING TUMOR: BLADDER

| | ANTIBODY | | | | | | | | | | | |
|---|---|---|---|---|---|---|---|---|---|---|---|---|
| | T16 | JP165 | J233 | T23 | T101 | T43 | T87 | J143 | T138 | T110 | Om37 | Om5 |
| Normal Kidney | | | | | | | | | | | | |
| KT | 0 | 0 | 0 | 0 | 0 | 3 | 3 | 3 | 3 | 2 | | |
| KM | 0 | | 0 | 0 | 0 | 3 | 3 | | 3 | 0 | | |
| KY | 3 | | 0 | 0 | 0 | 3 | 3 | | 2 | 0 | | |
| LB | 3 | | 0 | 0 | 3 | 3 | 3 | | 3 | | | |
| LC | 3 | | 0. | 0 | 0 | 3 | 3 | | 3 | 0 | | |
| LD | 3 | | 0 | 0 | 0 | 3 | 3 | | 2 | 0 | | |
| LE | 3 | | 0 | 0 | 0 | 3 | 3 | | 3 | 0 | | |
| LN | 0 | 1 | 0 | 0 | 1 | 0 | 0 | 3 | 2 | 0 | | |

TABLE II-continued
REACTION OF MONOCLONAL ANTIBODIES PRODUCED FROM HUMAN BLADDER TUMOR IMMUNOGEN WITH NORMAL HUMAN CELL LINES
IMMUNIZING TUMOR: BLADDER
ANTIBODY

|  | T16 | JP165 | J233 | T23 | T101 | T43 | T87 | J143 | T138 | T110 | Om37 | Om5 |
|---|---|---|---|---|---|---|---|---|---|---|---|---|
| KN | 3 | 0 | 0 | 0 | 0 | 0 | 2 | 3 | 3 | 3 | 0 |  |
| LI | 3 | 0 | 0 | 0 | 3 | 3 | 3 | 3 | 3 | 0 |  |  |
| LJ | 3 | 0 | 0 | 0 | 3 | 3 | 3 | 3 | 3 | 0 |  |  |
| MN | 2 | 0 | 0 | 0 | 0 | 0 | 3 | 3 | 2 |  | 0 | 0 |
| MQ | 2 | 0 | 0 | 0 | 0 | 0 | 3 | 3 | 2 |  | 0 | 0 |
| MP | 3 | 0 | 0 | 0 | 0 | 2 | 3 | 3 | 3 |  | 0 | 0 |
| MV | 3 | 0 | 0 | 0 | 2 | 2 | 3 | 3 | 2 |  | 0 | 0 |
| MS | 0 | 0 | 0 | 0 | 0 | 0 | 3 | 3 | 2 |  | 0 | 0 |
| Fibroblasts |  |  |  |  |  |  |  |  |  |  |  |  |
| Karper | 0 | 0 | 0 |  | 0 | 0 | 3 | 0 | 0 |  | 0 | 0 |
| Moroff | 0 | 0 | 0 |  | 0 | 0 | 0 | 3 | 0 |  | 0 | 0 |
| Migdol | 0 | 0 | 0 |  | 0 | 0 | 2 | 3 | 0 |  | 0 | 0 |
| Viola | 0 | 0 | 0 |  | 0 | 0 | 3 | 3 | 0 |  | 0 | 0 |
| EBV-Lymphocytes |  |  |  |  |  |  |  |  |  |  |  |  |
| DX | ∅ | ∅ |  | ∅ |  |  |  |  |  |  |  |  |
| AZ | ∅ | ∅ |  | ∅ |  | ∅ |  |  | ∅ |  | ∅ | ∅ |
| BD | ∅ | ∅ |  | ∅ |  | ∅ |  |  | ∅ |  | ∅ | ∅ |
| AV | ∅ | ∅ |  | ∅ | ∅ | ∅ |  |  | ∅ |  | ∅ | ∅ |
| FG | ∅ | ∅ |  |  |  | ∅ |  |  | ∅ | ∅ | ∅ | ∅ |
| Erythrocytes |  |  |  |  |  |  |  |  |  |  |  |  |
| A+ | ∅ | ∅ | ∅ | ∅ | ∅ | ∅ | ∅ | ∅ | ∅ |  | ∅ | ∅ |
| B+ | ∅ | ∅ | ∅ | ∅ | ∅ | ∅ | ∅ | ∅ | ∅ |  | ∅ | ∅ |
| O+ | ∅ | ∅ | ∅ | ∅ | ∅ | ∅ | ∅ | ∅ | ∅ |  | ∅ | ∅ |
| SRBC | ∅ | ∅ | ∅ | ∅ | ∅ | ∅ | ∅ | ∅ | ∅ |  | ∅ | ∅ |

Legend to Table II
Serological reaction of bladder panel monoclonal antibodies with normal human cell lines. Tests same as for Table I except 0 indicates no reaction where only the absorption test was done.

TABLE III
TISSUE DISTRIBUTION OF THE MONOCLONAL ANTIBODIES OF THE BLADDER

|  | T16 | T87 | T43 | J143 | OM5 | OM37 | T101 | JP165 | J233 | T138 | T110 | T23 |
|---|---|---|---|---|---|---|---|---|---|---|---|---|
| A. FETAL TISSUES |  |  |  |  |  |  |  |  |  |  |  |  |
| Bladder Ca |  |  |  |  |  |  |  |  |  |  |  |  |
| LUNG | − | − | − | − | − | − | − | − | − | − | + | + |
| Bronchial Epithelium | − | − | − | − | − | − | − | − | − | − | − | − |
| Cartilage | − | − | − | − | − | − | − | − | − | − | − | + |
| Pneumocytes | − | − | − | − | − | − | − | − | − | − | − | − |
| Connect. Tis | − | − | − | − | − | − | − | − | − | − | + | + |
| HEART | − | − | − | − | − | − | − | − | − | − | − | − |
| THYMUS | − | − | − | − | − | − | − | − | − | − | − | + |
| Hassal's C. | − | − | − | − | − | − | − | − | − | − | − | − |
| Thymocytes | − | − | − | − | − | − | − | − | − | − | − | + |
| SPLEEN | − | − | − | − | − | − | − | − | − | − | − | + |
| White Pulp | − | − | − | − | − | − | − | − | − | − | − | + |
| Red Pulp | − | − | − | − | − | − | − | − | − | − | − | − |
| LIVER | − | − | − | − | − | − | − | − | − | − | + | − |
| Hepatocytes | − | − | − | − | − | − | − | − | − | − | − | − |
| Biliary Epi. Cells | − | − | − | − | − | − | − | − | − | − | − | − |
| GALLBLAD | − | − | − | ± | − | − | − | − | − | − | − | − |
| ESOPHAGUS | − | − | + | ± | − | − | − | − | − | − | − | − |
| STOMACH | − | − | − | − | − | − | − | − | − | − | − | − |
| SMALL INT. | − | − | − | − | − | − | − | − | − | − | − | − |
| COLON | − | + | − | − | − | − | − | − | − | − | − | − |
| PANCREAS | − | − | − | − | − | − | − | − | − | − | − | − |
| Exocrine | − | − | − | − | − | − | − | − | − | − | − | − |
| Endocrine | − | − | − | − | − | − | − | − | − | − | − | − |
| KIDNEY | + | + | + | + | − | − | − | − | − | + | + | − |
| Glomerulus | − | − | − | + | − | − | − | − | − | + | − | − |
| Prox. Tub. | − | − | + | − | − | − | − | − | − | − | − | − |
| Distal Tub. | + | + | − | − | − | − | − | − | − | − | − | − |
| Collec. Tub. | + | + | − | − | − | − | − | − | − | − | − | − |
| URETER | + | + | − | ± | − | − | − | − | − | − | − | − |
| UR. BLAD. | + | + | − | ± | − | − | − | − | − | − | − | − |
| ADRENAL | − | − | − | − | − | − | − | − | − | − | − | − |
| Cortex | − | − | − | − | − | − | − | − | − | − | − | − |
| Medulla | − | − | − | − | − | − | − | − | − | − | − | − |
| TESTES | − | − | − | − | − | − | − | − | − | − | − | + |
| Germ. Cells | − | − | − | − | − | − | − | − | − | − | − | − |
| Endoc. Cel. | − | − | − | − | − | − | − | − | − | − | − | − |
| Connect. T. | − | − | − | − | − | − | − | − | − | − | − | + |

TABLE III-continued
TISSUE DISTRIBUTION OF THE MONOCLONAL ANTIBODIES OF THE BLADDER

| | T16 | T87 | T43 | J143 | OM5 | OM37 | T101 | JP165 | J233 | T138 | T110 | T23 |
|---|---|---|---|---|---|---|---|---|---|---|---|---|
| OVARY | − | − | − | − | − | − | − | − | − | − | − | + |
| Germ. Cells | − | − | − | − | − | − | − | − | − | − | − | − |
| Connect.T. | − | − | − | − | − | − | − | − | − | − | − | + |
| FALLOP. T. | − | − | − | − | − | − | − | − | − | − | − | − |
| UTERUS | − | + | + | + | − | − | − | − | − | − | − | − |
| Endometrium | − | + | + | − | − | − | − | − | − | − | − | − |
| Myometrium | − | − | − | − | − | − | − | − | − | − | − | − |
| CERVIX | − | + | + | + | − | − | − | − | − | − | − | − |
| Endocervix | − | + | + | − | − | − | − | − | − | − | − | − |
| Exocervix | − | − | ± | − | − | − | − | − | − | − | − | − |
| SKIN | + | − | − | + | − | − | − | − | − | − | + | + |
| Epidermis | ± | − | − | − | − | − | − | − | − | − | − | − |
| Melanocytes | − | − | − | − | − | − | − | − | − | − | − | + |
| Sweat Gld. | − | − | − | − | − | − | − | − | − | − | − | − |
| Sebac. Gld. | − | − | − | − | − | − | − | − | − | − | − | − |
| Hair Fol. | − | − | − | − | − | − | − | − | − | − | − | − |
| Dermis C.T. | − | − | − | + | − | − | − | − | − | − | + | + |
| BRAIN | − | − | − | − | − | − | − | − | − | − | − | + |
| Neurons | − | − | − | − | − | − | − | − | − | − | − | − |
| Glial Cells | − | − | − | − | − | − | − | − | − | − | − | + |
| Dendrites | − | − | − | − | − | − | − | − | − | − | − | − |
| LYMPH NODE | − | − | − | − | − | − | − | − | − | − | − | + |
| BLOOD VES. | − | − | − | − | − | − | − | − | − | + | − | − |
| Endoth. Cel | − | − | − | − | − | − | − | − | − | + | − | − |
| Smooth Ms. | − | − | − | − | − | − | − | − | − | − | − | − |
| SOFT TIS. | − | − | − | − | − | − | − | − | − | − | + | + |
| SECRETION | − | − | − | − | − | − | − | − | − | − | − | − |
| B. ADULT TISSUES | | | | | | | | | | | | |
| LUNG | − | − | − | − | − | − | − | − | − | − | + | + |
| Bronchial Epithelium | − | − | − | − | − | − | − | − | − | − | − | − |
| Cartilage | − | − | − | − | − | − | − | − | − | − | − | + |
| Glandular Epithelium | − | − | − | − | − | − | − | − | − | − | − | − |
| Pneumocytes | − | − | − | − | − | − | − | − | − | − | − | − |
| Connect.Tis | − | − | − | − | − | − | − | − | − | − | + | + |
| HEART (ms) | − | − | − | − | − | − | − | − | − | − | − | − |
| SPLEEN | − | − | − | − | − | − | − | − | − | − | + | + |
| White Pulp | − | − | − | − | − | − | − | − | − | − | − | + |
| Red Pulp | − | − | − | − | − | − | − | − | − | − | − | − |
| LIVER | − | − | − | − | − | − | − | − | − | − | + | − |
| Hepatocytes | − | − | − | − | − | − | − | − | − | − | − | − |
| Bil. Epi. | − | − | − | − | − | − | − | − | − | − | − | − |
| Sinusoids | − | − | − | − | − | − | − | − | − | − | − | − |
| GALLBLAD | − | − | − | − | − | − | − | − | − | − | ± | − |
| ESOPHAGUS | + | − | ± | ± | − | − | − | − | − | − | ± | − |
| STOMACH | − | − | − | − | − | − | − | − | − | − | ± | − |
| SMALL INT. | − | − | − | − | − | − | − | − | − | − | ± | − |
| COLON | − | + | − | − | − | − | − | − | − | − | ± | − |
| G.I. Smc | − | − | − | − | − | − | − | − | − | − | − | − |
| PANCREAS | − | − | − | − | − | − | − | − | − | − | + | − |
| Exocrine | − | − | − | − | − | − | − | − | − | − | − | − |
| Endocrine | − | − | − | − | − | − | − | − | − | − | − | − |
| KIDNEY | + | + | + | + | − | − | − | − | − | + | + | − |
| Glomerulus | − | − | − | + | − | − | − | − | − | + | − | − |
| Prox. Tub. | − | − | + | − | − | − | − | − | − | − | − | − |
| Henle's L. | − | − | − | − | − | − | − | − | − | − | − | − |
| Distal Tub. | + | + | − | − | − | − | − | − | − | − | − | − |
| Collec. Tub. | + | + | − | − | − | − | − | − | − | − | − | − |
| URETER | + | + | − | ± | − | − | − | − | − | − | ± | − |
| UR. BLAD. | + | + | − | ± | − | − | − | − | − | − | ± | − |
| ADRENAL | − | − | − | − | − | − | − | − | − | − | − | − |
| Cortex | − | − | − | − | − | − | − | − | − | − | − | − |
| Medulla | − | − | − | − | − | − | − | − | − | − | − | − |
| THYROID | − | ± | − | + | − | − | − | − | − | − | − | − |
| Epithelium | − | ± | − | − | − | − | − | − | − | − | − | − |
| Colloid | − | − | − | − | − | − | − | − | − | − | − | − |
| BREAST | + | + | − | + | − | − | − | − | − | − | + | + |
| Duct. Cells | + | + | − | − | − | − | − | − | − | − | − | − |
| Acinar Cel. | − | + | − | − | − | − | − | − | − | − | − | − |
| Connec.Tis. | − | − | − | + | − | − | − | − | − | − | + | + |
| PROSTATE | − | ± | − | − | − | − | − | − | − | − | + | + |
| Epithelium | − | ± | − | − | − | − | − | − | − | − | − | − |
| Stroma | − | − | − | − | − | − | − | − | − | − | + | + |
| TESTES | − | − | − | − | − | − | − | − | − | − | + | + |
| Germ Cells | − | − | − | − | − | − | − | − | − | − | − | − |
| Endocrine Cells | − | − | − | − | − | − | − | − | − | − | − | − |
| Connec.Tis. | − | − | − | − | − | − | − | − | − | − | + | + |

TABLE III-continued
TISSUE DISTRIBUTION OF THE MONOCLONAL ANTIBODIES OF THE BLADDER

| | T16 | T87 | T43 | J143 | OM5 | OM37 | T101 | JP165 | J233 | T138 | T110 | T23 |
|---|---|---|---|---|---|---|---|---|---|---|---|---|
| OVARY | − | − | − | − | − | − | − | − | − | − | + | + |
| Germ Cells | − | − | − | − | − | − | − | − | − | − | − | − |
| Connec.Tis. | − | − | − | − | − | − | − | − | − | − | + | + |
| FALLOP.TUB. | − | − | − | − | − | − | − | − | − | − | − | − |
| UTERUS | − | + | − | − | − | − | − | − | − | − | + | − |
| Endometrium | − | + | − | − | − | − | − | − | − | − | − | − |
| Myometrium | − | − | − | − | − | − | − | − | − | − | − | − |
| CERVIX | + | + | + | + | − | − | − | − | − | − | + | − |
| Endocervix | − | + | − | − | − | − | − | − | − | − | − | − |
| Exocervix | + | − | ± | ± | − | − | − | − | − | − | − | − |
| PLACENTA | − | − | − | − | − | − | − | − | − | − | + | − |
| Cytotrophb. | − | − | − | − | − | − | − | − | − | − | − | − |
| Syncytotrb. | − | − | − | − | − | − | − | − | − | − | − | − |
| Sinusoids | − | − | − | − | − | − | − | − | − | − | − | − |
| SKIN | + | − | − | + | − | − | − | − | − | − | + | + |
| Epidermis | + | − | − | − | − | − | − | − | − | − | − | − |
| Melanocytes | − | − | − | − | − | − | − | − | − | − | − | + |
| Sweat Gld. | − | − | − | − | − | − | − | − | − | − | − | − |
| SebaceousG. | − | − | − | − | − | − | − | − | − | − | − | − |
| Dermis CT | − | − | − | − | − | − | − | − | − | − | + | + |
| BRAIN | − | − | − | − | − | − | − | − | − | − | − | + |
| Neurons | − | − | − | − | − | − | − | − | − | − | − | − |
| Glial Cells | − | − | − | − | − | − | − | − | − | − | − | + |
| Dendrites | − | − | − | − | − | − | − | − | − | − | − | − |
| LYMPH NODE | − | − | − | − | − | − | − | − | − | − | − | + |
| Fol/Medul | − | − | − | − | − | − | − | − | − | − | − | ± |
| BLOOD VES. | − | − | − | − | − | − | − | − | − | + | − | − |
| Endothelium | − | − | − | − | − | − | − | − | − | + | − | − |
| Smooth Ms. | − | − | − | − | − | − | − | − | − | − | − | − |
| CAPILLARIES | − | − | − | − | − | − | − | − | − | + | − | − |
| SKELETAL MS | − | − | − | − | − | − | − | − | − | − | − | − |
| SOFT TISSUE | − | − | − | − | − | − | − | − | − | − | + | + |
| SECRETIONS | − | − | − | − | − | − | − | − | − | − | − | − |

Legend to Table III
Immunopathology reaction of bladder panel monoclonal antibodies with fetal and adult normal human tissues in frozen section by indirect immunofluorescence.
− = no reaction
± = heterogeneous reaction within the tissue
+ = homogeneous positive reaction within the tissue
e.g. heterogeneous reaction is found with mAb J143 which reacts only with basal epithelial cells of normal urothelium.

TABLE III. A
REACTIVITY OF MOUSE MONOCLONAL ANTIBODIES GENERATED AGAINST BLADDER TUMORS. IMMUNOFLUORESCENCE TESTS WITH FROZEN SECTIONS OF NORMAL HUMAN FETAL (F)* AND ADULT (A) TISSUES.

| | Om5 | | T16 | | T87 | | J143 | | T43 | | T138 | | T23 | | JP165 | | T101 | | J233 | | T110 | |
|---|---|---|---|---|---|---|---|---|---|---|---|---|---|---|---|---|---|---|---|---|---|---|
| Human Tissues | F | A | F | A | F | A | F | A | F | A | F | A | F | A | F | A | F | A | F | A | F | A |
| Kidney | | | | | | | | | | | | | | | | | | | | | | |
| glomerus | 0 | 0 | 0 | 0 | 0 | 0 | ● | ● | 0 | 0 | 0 | 0 | 0 | 0 | 0 | 0 | 0 | 0 | 0 | 0 | 0 | 0 |
| proximal t. | 0 | 0 | 0 | 0 | 0 | 0 | 0 | 0 | ● | ● | 0 | 0 | 0 | 0 | 0 | 0 | 0 | 0 | 0 | 0 | 0 | 0 |
| distal t. | 0 | 0 | ● | ● | ● | ● | 0 | 0 | 0 | 0 | 0 | 0 | 0 | 0 | 0 | 0 | 0 | 0 | 0 | 0 | 0 | 0 |
| Urotnelium | 0 | 0 | ● | ● | ● | ● | ●+ | ●+ | 0 | 0 | 0 | 0 | 0 | 0 | 0 | 0 | 0 | 0 | 0 | 0 | 0 | 0 |
| Prostate | ● | 0 | ● | ● | ● | ● | | 0 | | 0 | | 0 | | 0 | | 0 | | 0 | | 0 | | 0 |
| Testes | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Ovary | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Uterus | | | | | | | | | | | | | | | | | | | | | | |
| exocervix | | 0 | | ● | | 0 | | 0 | | ●+ | | 0 | | 0 | | 0 | | 0 | | 0 | | 0 |
| endocervix | | 0 | | 0 | | ● | | 0 | | 0 | | 0 | | 0 | | 0 | | 0 | | 0 | | 0 |
| endometrium | 0 | 0 | 0 | 0 | ● | ● | 0 | 0 | 0 | 0 | 0 | 0 | 0 | 0 | 0 | 0 | 0 | 0 | 0 | 0 | 0 | 0 |
| Fallopain tubes | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Placenta | | 0 | | 0 | | 0 | | 0 | | 0 | | 0 | | 0 | | 0 | | 0 | | 0 | | 0 |
| Breast | | | | | | | | | | | | | | | | | | | | | | |
| ducts | | 0 | | ● | | | | ● | | 0 | | 0 | | 0 | | 0 | | 0 | | 0 | | 0 |
| acini | | 0 | | 0 | | | | ● | | 0 | | 0 | | 0 | | 0 | | 0 | | 0 | | 0 |
| Skin | | | | | | | | | | | | | | | | | | | | | | |
| epidermis | 0 | 0 | ● | ● | 0 | 0 | ●+ | ●+ | ●+ | ●+ | 0 | 0 | 0 | 0 | 0 | 0 | 0 | 0 | 0 | 0 | 0 | 0 |
| adnexa | 0 | 0 | ● | ● | 0 | 0 | 0 | 0 | 0 | 0 | 0 | 0 | 0 | 0 | 0 | 0 | 0 | 0 | 0 | 0 | 0 | 0 |
| melanocytes | | 0 | | 0 | | 0 | | 0 | | 0 | | 0 | ● | 0 | | 0 | | 0 | | 0 | | 0 |
| Brain | | 0 | | 0 | | 0 | | 0 | | 0 | | 0 | ● | 0 | | 0 | | 0 | | 0 | | 0 |
| Heart | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lung | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Esophagus | 0 | 0 | ● | ● | 0 | 0 | ●+ | ●+ | ●+ | ●+ | 0 | 0 | 0 | 0 | 0 | 0 | 0 | 0 | 0 | 0 | 0 | 0 |
| Stomach | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Small Intestine | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Colon | 0 | 0 | 0 | 0 | ● | ● | 0 | 0 | 0 | 0 | 0 | 0 | 0 | 0 | 0 | 0 | 0 | 0 | 0 | 0 | 0 | 0 |
| Liver | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE III. A-continued

REACTIVITY OF MOUSE MONOCLONAL ANTIBODIES GENERATED AGAINST BLADDER TUMORS.
IMMUNOFLUORESCENCE TESTS WITH
FROZEN SECTIONS OF NORMAL HUMAN FETAL (F)* AND ADULT (A) TISSUES.

| Human Tissues | Om5 F | Om5 A | T16 F | T16 A | T87 F | T87 A | J143 F | J143 A | T43 F | T43 A | T138 F | T138 A | T23 F | T23 A | JP165 F | JP165 A | T101 F | T101 A | J233 F | J233 A | T110 F | T110 A |
|---|---|---|---|---|---|---|---|---|---|---|---|---|---|---|---|---|---|---|---|---|---|---|
| Pancreas | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Thyroid | | 0 | | 0 | | ● | | ● | | 0 | | 0 | | 0 | | 0 | | 0 | | 0 | | 0 |
| Adrenal | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lymph Node | | 0 | | 0 | | 0 | | 0 | | 0 | | 0 | | ӫ | | 0 | | 0 | | 0 | | |
| Spleen | 0 | 0 | 0 | 0 | 0 | 0 | 0 | 0 | 0 | 0 | 0 | 0 | ● | ● | 0 | 0 | 0 | 0 | 0 | 0 | 0 | 0 |
| Thymus | 0 | | 0 | | ӫ | | 0 | | | | ӫ | 0 | | ӫ | | 0 | | 0 | | 0 | | 0 |
| Extracellular Matrix | 0 | 0 | 0 | 0 | 0 | 0 | ӫ | ӫ | 0 | 0 | 0 | 0 | 0 | 0 | 0 | 0 | 0 | 0 | 0 | 0 | | ● |
| Fibroblasts | 0 | 0 | 0 | 0 | 0 | 0 | 0 | 0 | 0 | 0 | 0 | 0 | ● | ● | 0 | 0 | 0 | 0 | 0 | 0 | 0 | 0 |
| Smooth Muscle | 0 | 0 | 0 | 0 | 0 | 0 | 0 | 0 | 0 | 0 | 0 | 0 | ● | ● | 0 | 0 | 0 | 0 | 0 | 0 | 0 | 0 |
| Striated Muscle | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cartilage | 0 | 0 | 0 | 0 | 0 | 0 | 0 | 0 | 0 | 0 | 0 | 0 | ● | ● | 0 | 0 | 0 | 0 | 0 | 0 | 0 | 0 |
| Endothelial Cells | 0 | 0 | 0 | 0 | 0 | 0 | 0 | 0 | 0 | 0 | ● | ● | 0 | 0 | 0 | 0 | 0 | 0 | 0 | 0 | 0 | 0 |

*Fetal tissues obtained from a 14-wk-old fetus.
Reactivity of monoclonal antibodies with tissue sections is symbolized as follows:
0, no immunofluorescence;
●, immunofluorescence;
ӫ, heterogenous pattern of immunofluorescence.
+, positive on the basal cell layer only.

TABLE IV

Immunoanatomical study of bladder panel of monoclonal antibodies on frozen sections of human tumors

| HUMAN TUMORS TESTED | | MONOCLONAL ANTIBODIES[d] | | | | | | | | | | |
|---|---|---|---|---|---|---|---|---|---|---|---|---|
| | | Om5 | Om37 | T16 | T87 | J143 | T43 | T101 | JP165 | J233 | T23 | T138 |
| BLADDER | (10) | 4 | 4 | 9 | 9 | 10 | 6 | 4 | 2 | — | 3 | 5 |
| RENAL | (8) | — | — | — | — | — | 3 | — | 2 | — | 2 | — |
| COLON | | | | | | | | | | | | |
| Adenomatous Polyp | (1) | — | — | — | 1 | 1 | — | — | — | — | — | — |
| Villous adenoma | (1) | — | — | — | 1 | 1 | — | 1 | — | — | — | — |
| Adenocarcinoma | (2) | — | — | — | 2 | 2[b] | 2 | — | — | — | — | — |
| LUNG | | | | | | | | | | | | |
| Carcinoid | (1) | — | — | — | 1 | — | — | — | — | — | — | — |
| Epidermoid Cancer | (3) | — | — | 2[a] | 2[b] | 3[b] | 3 | — | — | — | 3[b] | 2[b] |
| Oat cell carcinoma | (1) | — | — | — | 1 | 1[b] | 1 | — | — | — | — | — |
| BREAST | | | | | | | | | | | | |
| Fibroadenoma | (2) | — | — | 2 | 2 | 1 | — | — | — | — | — | 1[c] |
| Adenocarcinomas | (3) | — | — | 3 | 3 | 2 | 3 | 1[b] | — | — | 3[b] | 1[c] |
| MELANOMA | (2) | — | — | — | — | — | — | — | — | — | 2 | — |
| ASTROCYTOMA | (2) | — | — | — | — | — | 1 | — | — | — | 2 | 2[b] |
| HODGKIN | (1) | — | — | — | 1[b] | — | 1 | — | — | — | — | — |
| LYMPHOMA | (1) | — | — | — | 1[b] | — | 1 | — | — | — | — | — |
| TERATOCARCINOMA (testicular) | (2) | — | — | — | 2 | 2 | 2 | — | — | — | 2 | — |

[a]On areas of well differentiated squamous carcinoma only.
[b]Heterogeneous reactivity - positive on subpopulations of cells only.
[c]Positive on the lining of cystic areas only.
[d]T110 monoclonal antibody was positive in the interstitial tissue of all the tumors with variable intensity.
Legend to Table IV
Immunopathological reaction of bladder panel monoclonal antibodies with human cancer tissues in frozen sections by indirect immunofluorescence.
The numbers listed under mAbs indicate the number of human tumor specimans of a given type that give a positive reaction with indirect immunofluorescence. The number of tumors tested is indicated in parentheses.

TABLE IV.A

REACTIVITY OF MOUSE MONOCLONAL ANTIBODIES GENERATED AGAINST BLADDER TUMORS.
IMMUNOFLUORESCENCE TESTS WITH FROZEN SECTIONS OF HUMAN TUMORS.

| HUMAN TUMORS | No. of specimens | MONOCLONAL ANTIBODIES | | | | | | | | |
|---|---|---|---|---|---|---|---|---|---|---|
| | | Om5 | T16 | T87 | J143 | T43 | T138* | T23 | JP165 | T101 | J233 |
| BLADDER | 10 | 4 | 9 | 9 | 10 | 6 | 5 | 3 | 2 | 4 | — |
| RENAL | 8 | — | — | 1 | — | 3 | — | 2 | 2 | — | — |
| COLON | | | | | | | | | | | |
| Adenomatous polyp | 1 | — | — | 1 | 1 | — | — | — | — | — | — |
| Villous adenoma | 1 | — | — | 1 | 1 | — | — | — | — | 1 | — |
| Adenocarcinoma | 2 | — | — | 2 | 2++ | 2 | — | — | — | — | — |
| LUNG | | | | | | | | | | | |
| Carcinoid | 1 | — | — | 1 | — | — | — | — | — | — | — |
| Epidermoid cancer | 3 | — | 2+ | 2++ | 3++ | 3 | 2++ | 3++ | — | — | — |
| Oat cell carcinoma | 1 | — | — | 1 | 1++ | 1 | — | — | — | — | — |

TABLE IV.A-continued
REACTIVITY OF MOUSE MONOCLONAL ANTIBODIES GENERATED AGAINST BLADDER TUMORS. IMMUNOFLUORESCENCE TESTS WITH FROZEN SECTIONS OF HUMAN TUMORS.

| HUMAN TUMORS | No. of specimens | MONOCLONAL ANTIBODIES | | | | | | | | | |
|---|---|---|---|---|---|---|---|---|---|---|---|
| | | Om5 | T16 | T87 | J143 | T43 | T138* | T23 | JP165 | T101 | J233 |
| BREAST | | | | | | | | | | | |
| Fibroadenoma | 2 | — | 2 | 2 | 1 | — | 1 | — | — | — | — |
| Adenocarcinoma | 3 | — | 3 | 3 | 2 | 3 | 1 | 3++ | — | 1++ | — |
| ASTROCYTOMA | 2 | — | — | — | — | 1 | — | 2 | — | — | — |
| MELANOMA | 2 | — | — | — | — | — | — | 2 | — | — | — |
| SARCOMA | 3 | — | — | — | — | 2 | 1 | 3 | — | — | — |
| LYMPHOMA | 2 | — | — | 2++ | — | 2 | — | — | — | — | — |
| TERATO-CARCINOMA (testicular) | 2 | — | — | 2 | 2 | 2 | — | 2 | — | — | — |

*endothelial cells of all tumor specimens positive.
+areas of well differentiated squamous carcinoma only.
++heterogenous reactivity - subpopulations of cells only. lining of cystic areas only.
—: no immunofluorescence of tumor cells.

TABLE V
ABSORPTION ANALYSIS

| CELLS | MONOCLONAL ANTIBODIES | | |
|---|---|---|---|
| | T16* | Om5** | T43* |
| SK-MEL-28 | — | ⊕ | ⊕ |
| T-24 | ⊕ | — | ⊕ |
| Papillary Bladder Tumor | ⊕ | ⊕ | — |
| Normal Bladder Urothelium | ⊕ | — | — |

*T16 and T43 were tested on T-24 cells
**Om5 was tested on SK-MEL-28

What is claimed:

1. Method for differentiating between normal and malignant human transitional bladder cells and between invasive and non-invasive bladder transitional cell carcinomas which comprises contacting a shed or intact human bladder transitional cell specimen with at least two of the monoclonal antibodies selected from the group consisting of T16, T23, T43, J233, JP165, T101, Om5, Om37, J143, T87, T138 and T110 and detecting malignant transitional bladder cells and distinguishing between invasive and non-invasive malignant transitional bladder cells reacting with said antibodies.

2. Method for differential diagnosis of malignant human bladder transitional cells which comprises contacting a shed or intact human bladder cell specimen with at least two of the monoclonal antibodies selected from the group consisting of T16, T23, T43, J233, JP165, T101, Om5, Om37, J143, T87, T138 and T110 and distinguishing invasive from non-invasive malignant transitional bladder cells and further distinguishing malignant bladder carcinoma from malignant bladder sarcoma reacting with said antibodies.

3. Method of claim 2 wherein said specimenm is separately or sequentially contacted with a panel of two or more of said monoclonal antibodies each of which is different.

4. Method of claim 2 wherein non-invasive bladder transitional cell tumors are distinguished from invasive bladder transitional cell carcinomas using monoclonal antibody selected from the group consisting of Om5, Om37 and T43.

5. Method of claim 2 wherein transitional cell bladder carcinomas are distinguished from bladder sarcomas using monoclonal antibodies selected from the group consisting of Om37, T16, T87, J143 and T43.

6. A panel of monoclonal antibodies derived from immunization with human bladder transitional cell carcinoma cells or human bladder papilloma extracts wherein said panel is capable of restricted and nonrestricted immunological reaction with, shed and intact human bladder transitional cells antigen, further capable of distinguishing invasive from non-invasive bladder transitional cell carcinoma, further capable of distinguishing human bladder transitional cell carcinoma from bladder sarcoma and wherein the panel members consist of at least two monoclonal antibodies selected from the group consisting of T16, T23, J233, JP165, T101, T43, J143, T87, T138, T101, Om37 and Om5.

7. Monoclonal antibody producing hybridoma cell lines characterized by the production of the monoclonal antibodies of the panel of claim 6.

8. Monoclonal antibodies of claim 6 recognizing human bladder transitional epithelial antigens selected from the group of glycoproteins, glycolipids and proteins.

9. Monoclonal antibodies of claim 8 wherein the glycoprotein molecular weight range is approximately 25–240 kd.

10. Monoclonal antibodies of claim 9 wherein the glycoprotein antigens are selected from the molecular weight group consisting of 48 kd, 85 kd, 60 kd, 80 kd, 30 kd, 120 kd, 25 kd, 140 kd, 240 kd.

* * * * *